United States Patent
Hirsch et al.

(10) Patent No.: US 7,734,077 B2
(45) Date of Patent: ***Jun. 8, 2010

(54) METHOD OF ASSESSING LOCALIZED SHAPE AND TEMPERATURE OF THE HUMAN BODY

(75) Inventors: Raphael Hirsch, Pittsburgh, PA (US);
James Osborn, Oakmont, PA (US);
Chian Kent Kwoh, Pittsburgh, PA (US);
Louis J. Denes, Pittsburgh, PA (US);
Daniel Huber, Pittsburgh, PA (US)

(73) Assignee: University of Pittsburgh - Of The Commonwealth System of Higher Education, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/395,912

(22) Filed: Mar. 2, 2009

(65) Prior Publication Data
US 2009/0216130 A1   Aug. 27, 2009

Related U.S. Application Data

(62) Division of application No. 11/223,565, filed on Sep. 9, 2005, now Pat. No. 7,519,210.

(60) Provisional application No. 60/608,507, filed on Sep. 9, 2004.

(51) Int. Cl.
*G06K 9/00* (2006.01)
*A61B 6/02* (2006.01)

(52) U.S. Cl. .......................... 382/128; 382/154; 378/41

(58) Field of Classification Search ................. 382/100, 382/103, 108, 128, 129, 130, 131, 133, 134, 382/168, 181, 193, 199, 203, 210, 224, 232, 382/274, 276, 285, 305, 154; 427/140; 280/33.991; 600/420, 416, 427, 474; 378/41
See application file for complete search history.

(56) References Cited

U.S. PATENT DOCUMENTS

| | | | |
|---|---|---|---|
| 6,640,130 B1 * | 10/2003 | Freeman et al. | 600/474 |
| 6,644,674 B2 * | 11/2003 | Simard | 280/33.991 |
| 6,711,432 B1 * | 3/2004 | Krause et al. | 600/427 |
| 6,901,282 B2 * | 5/2005 | Edelman | 600/420 |
| 6,905,727 B2 * | 6/2005 | Spitzer et al. | 427/140 |
| 7,184,814 B2 * | 2/2007 | Lang et al. | 600/416 |
| 7,339,908 B2 * | 3/2008 | Uhlik et al. | 370/331 |

OTHER PUBLICATIONS

Anderson et al., "Which Traditional Measures Should Be Used in Rheumatoid Arthritis Clinical Trials?", Arthritis and Rheumatism, Sep. 1989, vol. 32, No. 9, pp. 1093-1099.

(Continued)

*Primary Examiner*—Seyed Azarian
(74) *Attorney, Agent, or Firm*—Knobbe, Martens Olson & Bear LLP

(57) ABSTRACT

A method of objectively quantifying assessments of joints having arthritis for purposes of assessment, diagnosis and treatment. The objective measurements utilize known imaging modalities including 3D scanning, thermal imaging, visible and near-infrared imaging and two-dimensional imaging to quantify swelling, heat distribution, erythema, and range or motion. The objective measurements can be combined in various ways to assess the extent of the disease and can be used to adjust treatment protocols.

22 Claims, 15 Drawing Sheets

OTHER PUBLICATIONS

Hammer et al, "Standardized Percentile Curves of Body-Mass Index for Children and Adolescents", AJDC, Mar. 1991, vol. 145, pp. 259-263.

De Silva et al., "Assessment of Inflamation in the Rheumatoid Knee Joint: Correlation Between Clinical, Radioisotopic, and Thermographic Methods", Annals of the Rheumatic Diseases, 1986, vol. 45, pp. 277-280.

Hall et al , "A Combined Clinical and Immunological Assessment of Four Cyclophosphamide Regimes in Rheumatoid Arthritis", Histamine and Immunology, Agents and Actions, 1979, vol. 9/1, pp. 97-102.

Ruperto et al., "Redundancy of Conventional Articular Response Variables Used in Juvenile Chronic Arthritis Clinical Trials", Annals of the Rheumatic Diseases, Jan. 1996, vol. 55(1), pp. 73-75.

Felson et al., "The American College of Rheumatology Preliminary Core SEt of Disease Activity Measures for Rheumatoid Arthritis Clinical Trials", Arthritis and Rheumatism, Jun. 1993, vol. 36, No. 6, pp. 729-740.

Will et al., "Infrared Thermography: What Is Its Place in Rheumatology in the 1990s?", British Journal of Rheumatology, 1992, vol. 31, pp. 337-334.

Felson, "Choosing a Core Set of Disease Activity Measures for Rheumatoid Arthritis Clinical Trials", The Journal of Rheumatology, 1993, vol, 20:3, pp. 531-534.

Dieppe et al., "Intra-Articular Steroids in Osteoarthritis", Rheumatology and Rehabilitation, 1980, vol. 19, pp. 212-217.

Varju et al , "Assessment of Hand Osteoarthritis: Correlation Between Thermographic and Radiographic Methods", Rheumatology, May 4, 2004, vol. 43, pp. 915-919.

Giannini et al., "Preliminary Definition of Improvement in Juvenile Arthritis", Arthritis and Rheumatism, Jul. 1997, vol. 40, No. 7, pp. 1202-1209.

Giannini et al., "FDA Draft Guidelines for the Clinical Evaluation of Antiinflammatory and Antirheumatic Drugs in Children", Arthritis and Rheumatism, May 1995, vol. 38, No. 5, pp. 715-718, 1995.

Bacon et al., "Thermography in the Assessment of Inflammatory Arthritis", Clinics in Rheumatic Diseases, Apr. 1976, vol. 2, No. 1, pp. 51-65.

Liang et al., "Longitudinal Data Analysis Using Generalized Linear Models", Biometrika, 1986, vol. 73, No. 1, pp. 13-22.

Collins et al., "Thermography and Radiology Complimentary Methods for the Study of Inflammatory Diseases", Clinical Radiology, 1976, vol. 27, pp. 237-243.

Graft et al , "Thermographic Characterization of Osteoarthrosis of the Temporomandibular Joint", Journal of Orofacial Pain, 1993, vol. 7, No. 4, pp. 345-353.

Bacon et al., "Thermography in the Assessment of Anti Rheumatic Agents", Rheumatoid Arthritis, 1977, pp. 105-110.

Devereaux et al., "Disease Activity Indexes in Rheumatoid Arthritis; A Prospective, Comparative Study with Thermography", Annals of the Rheumatic Diseases, 1985, vol. 44, pp. 434-437, 1985.

Ring et al., "The Thermographic Assessment of Inflammation and Anti-Inflammatory Drugs in Osteoarthritis", British Journal of Clinical Practice, Jun. 24, 1981, Fifteenth International Congress of Rheumatology, Paris—Jun. 27-27, 1981, pp. 263-264.

Ring et al , "Thermologic Methods in Clinical Pharmacology—Skin Temperature Measurement in Drug Trials", Int' Journal of Clinical Pharmacology, Therapy and Toxicology, 1984, 22:20.

Cleveland et al., "Regression by Local Fitting, Methods, Properties, and Computational Algorithms", Journal of Econometrics, 1988, vol. 37, pp. 87-114.

Huber et al., "Fully Automatic Registration of Multiple 3D Data Sets", Image and Vision Computing, 2003, vol. 21, pp. 637-650.

Hebert et al., "Outdoor Scene Analysis Using Range Data", Proceedings of 86 IEEE International Conference on Robotics and Automation, Apr. 7-10, 1986, San Francisco, pp. 1426-1432.

Carmicheal et al., "Shape-based Recognition of Wiry Objects", The Robotics Institute, Carnegie Mellon University (2003).

Herbert et al., "3-D Measurements From Imaging Laser Radars: How Good Are They?", IEEE/RJ International Workshop on Intelligent Robots and Systems IROS, Nov. 3-5, 1991, Osaka, Japan IEEE Cat. No. 91TH0375-6, pp. 359-364.

Herbert et al., "3-D Vision for Outdoor Navigation by an Autonomous Vehicle", In. Proc. of Image Understanding Workshop, Morgan Kaufmann Publ., Inc., Apr. 1988, pp. 593-601.

Huber et al., "Automated 3D Underground Mine Mapping", The 4th Int'l. Conference on Field and Service Robotics, Jul. 14-16, 2003.

Tsin et al., "Statistical Calibration of CCD Imaging Process", Appeared in the Proceedings of the IEEE 2001 Conference on Computer Vision, pp. 1-8.

Klinker et al., "A Physical Approach to Color Image Understanding", Int. Journal of Computer Vision, 1990, vol. 4, pp. 7-38.

Herbert, "Active and Passive Range Sensing for Robotics", Proceedings of the 2000 IEEE Int'l. Conference on Robotics & Automation, San Francisco, CA, Apr. 2000, pp. 102-110.

Giannini et al., "Methotrexate in Resistant Juvenile Rheumatoid Arthritis. Results of the U.S.A.-U.S.S.R. double-blind, placebo-controlled trial. The Pediatric Study Group and the Cooperative Children's Study Group", The New England Journal of Medicine, Apr. 16, 2002, vol. 326, No. 16.

Lovell et al., "Etanercept in Children with Polyarticular Juvenile Rheumatoid Arthritis", The New England Journal of Medicine, Mar. 16, 2000, vol. 342, No. 11, pp. 763-769.

Campbell et al., "A Survey of Free-Form Object Representation and Recognition Techniques", Computer Vision and Image Understanding, 2001, vol. 81, pp. 166-210.

Al-Matar et al , "The Early Pattern of Joint Involvement Predicts Disease Progression in Children with Oligoarticular (Pauciarticular) Juvenile Rheumatoid Arthritis", Arthritis and Rheumatism, Oct. 2002, vol. 46, No. 10, pp. 2708-2715.

Huber et al., "3D Modeling Using a Statistical Sensor Model and Stochastic Search", Proceedings of the IEEE Conference on Computer Vision and Pattern Recognition (CVPR), Jun. 2003, vol. 1, pp. 858-865.

Johnson et al., "Surface Registration by Matching Oriented Points", Appearing in the International Conference on Recent Advances in 3-D Imaging and Modeling, Ottawa, Ontario May 12-15, 1997.

Huber et al., "3-D Map Reconstruction from Range Data", Proceedings of the 2000 IEEE Int'l. Conference on Robotics & Automation, San Francisco, CA, Apr. 2000, pp. 891-897.

Johnson et al., "Using Spin Images for Efficient Object Recognition in Cluttered 3D Scenes", May 1999, vol. 21, No. 5, pp. 433-449.

Scharstein et al , "A Taxonomy and Evaluation of Dense Two-Frame Stereo Correspondence Algorithms", International Journal of Computer Vision, 2002, vol. 47(1/2/3) pp. 7-42.

Lovell et al , "Long-Term Efficacy and Safety of Etanercept in Children with Polyarticular-Course Juvenile Rheumatoid Arthritis, Interim Results From an Ongoing Multicenter, Open-Label, Extended-Treatment Trial", Arthritis and Rheumatism, Jan. 2003, vol. 48, No. 1, pp. 218-226.

Dzladzlo et al., Losartan Therapy for Raynaud's Phenomenon and Scleroderma, Clinical and Biochemical Findings in a Fifteen-Week, Randomized, Parallel-Group. Controlled Trial, Arthritis and Rheumatism, Dec. 1999, vol. 42, No. 12, pp. 2646-2655.

Bruehl et al., "Validation of Thermography in the Diagnosis of Reflex Sympathetic Dystrophy", The Clinical Journal of Pain, Dec. 1996, vol. 12(4), pp. 316-325.

Cherkas et al., "The Use of Portable Radiometry to Assess Raynaud's Phenomenon: A Practical Alternative to Thermal Imaging", Rheumatology, 2001, vol. 40, pp. 1384-1387.

Salisbury et al., "Heat Distribution Over Normal and Abnormal Joints: Thermal Pattern and Quantification", Annals of the Rheumatic Diseases, 1983, vol. 42, pp. 494-499.

Sagawa et al., "Robust and Adaptive Integration of Multiple Range Images with Photometric Attributes", Institute of Industrial Science, University of Toyko, pp. 1-8, 2001.

El-Hakim et al., "A System for Indoor 3-D Mapping and Virtual Environments", Institute for Information Technology, National Research Council, Ottawa, Ontario Canada K1A 0R6, 1997.

Neugebauer, "Reconstruction of Real-World Objects Via Simultaneous Registration and Robust Combination of Multiple Range Images", Int'l Journal of Shape Modeling, 1997, vol. 3, No. 1 & 2, pp. 71-90.

Curless et al., "A Volumetric Method for Building Complex Models from Range Images", pp. 1-10, 2002.

Ruiz-Correa, "A New Paradigm for Recognizing 3-D Object Shapes from Range Data", Proceedings of the Ninth IEEE International Conference on Computer Vision (ICCV 2003).

Yamany et al., "Surface Signatures: An Orientation Independent Free-Form Surface Representation Scheme for the Purpose of Objects Registration and Matching", IEEE Transactions on Pattern Analysis and Machine Intelligence, Aug. 2002, vol. 24, No. 8, pp. 1105-1120.

Lazebnik et al., "Affine-Invariant Local Descriptors and Neighborhood Statistics for Texture Recognition"; Proceedings of the Ninth IEEE International Conference on Computer Vision (ICCV 2003).

* cited by examiner

METHOD OF ASSESSING LOCALIZED SHAPE AND TEMPERATURE OF THE HUMAN BODY

CROSS-REFERENCE TO RELATED APPLICATIONS

This application is a divisional application of U.S. Utility application Ser. No. 11/223,565 filed Sep. 9, 2005 which claims benefit of U.S. Provisional Application 60/608,507, filed Sep. 9, 2004. The entire contents of U.S. Utility application Ser. No. 11/223,565 and U.S. Provisional Application No. 60/608,507 are incorporated by reference into this divisional utility application.

FIELD OF THE INVENTION

This invention relates to the field of medical assessment, and, in particular, relates to the measurement of localized body shape and temperature using sensor technology for purposes of assessing medical conditions and tracking treatment progress.

BACKGROUND OF THE INVENTION

Physicians diagnosing and treating disease involving inflammation of the joints, such as arthritis, including osteoarthritis (OA), rheumatoid arthritis (RA) or juvenile rheumatoid arthritis (JRA) have experienced difficulty in quantifying the extent of inflammation or establishing the diagnosis. A typical arthritis patient may present with one or more various symptoms relating to synovitis, including swelling, heat, redness and reduced mobility in one or more joints. However, it has proven remarkably difficult to measure these signs in arthritis patients in a consistent manner, or even to get agreement between rheumatologists as to the presence or absence of the disease in a given joint. Physician global assessment and assessment of swollen and/or tender joints are standard tools used to measure disease activity and response to therapy in clinical studies. Various components of these algorithms call for the unbiased, precise estimations of inflammation, as manifested by swelling, heat, erythema, pain on motion, tenderness and/or limitations of motion in the joints. Unfortunately, these measures are cumbersome, time-consuming, and often unreliable. Carefully designed studies have repeatedly shown poor reproducibility of these manifestations of synovitis. Both intra- and inter-rater reliability estimates show high coefficients of variations, and low correlation coefficients and intra-class correlations. Unfortunately, training workshops designed for "joint assessors" and conducted by experienced pediatric rheumatologists have had little impact in addressing this problem.

Partly because of the difficulty in accurately measuring joint inflammation, surrogate markers of inflammation and outcome measures for arthritis have been developed. As an example, the FDA and the American College of Rheumatology (ACR) have adopted the ACR 20/50/70 and the ACR Pediatric 30. These algorithms have gained widespread acceptance and are now used as the primary measure of response in both children and adults with inflammatory arthritis. The ACR algorithms include 6 core components: (1) physician global assessment of disease activity; (2) parent/patient assessment of overall well-being; (3) functional ability; (4) number of joints with active arthritis; (5) number of joints with limited range of motion; and (6) erythrocyte sedimentation rate (ESR), which is also included in the ACR 20/50/70. While components 1-3 require subjective assessments, either on the part of the patient or the physician, components 4-6 should be measurable and quantifiable. Tools that would produce a set of reliable, reproducible and objective measures of the inflammatory state of the joint would have at least two important benefits. First, they would improve assessment of outcome in clinical studies of arthritis by providing a more reliable measure of changes in synovitis in response to therapy. Second, they would be useful to the rheumatologist in the clinic by allowing objective comparison of a given patient's joints from visit to visit.

Improved objective measures of joint inflammation are clearly needed. Tools which could quantify the major components of the joint count assessment to develop a quantitative, highly reliable, time- and cost-efficient method of determining the major physical examination parameters of the joints would be highly desirable. Therefore, it is an object of this invention to develop tools for the objective measurement of various symptoms presented by arthritis patients.

SUMMARY OF THE INVENTION

The present invention utilizes various existing imaging sensor technologies, including 3D imaging, thermal imaging, near-infrared imaging and visual range imaging to quantify the major physical examination components of a joint. These include joint swelling 10, range of motion 20, heat distribution 30, and erythema (redness of the skin) 40, as shown in FIG. 1. This provides a highly-reproducible, consistent means of assessing the health of a joint and for tracking the effectiveness of treatment for arthritis, as well as for other applications requiring precise measurement of the body. In addition, because several components of the ACR 20/50/70 and the ACR Pediatric 30 algorithm rely on these objective measurements, the overall effectiveness and accuracy of these measure will be improved.

Swelling represents a change in the shape and volume of the soft tissues surrounding the joint. As such, the swelling is amenable to being quantified using established techniques for 3D imaging, shape measurement and volumetric analysis. Swelling can be detected as a subtle change in shape and volume through a 3D image collected using a 3D scanner, such as a laser line triangulation scanner, on a joint. Preferably, the joint is immobilized to minimize any movement during the scanning process, although it may not be necessary to utilize an apparatus to immobilize the joint.

In laser line triangulation, a laser line is scanned across the surface while a camera views the surface from a different vantage. Range is computed through triangulation by observing the position of the laser line on the surface at each point in time. Although a laser line triangulation scanner is used in the preferred embodiment, any 3D scanner capable of producing a 3D surface scan of the skin in sufficient detail may be used. The 3D scanner produces a digital representation of the surface shape of complex objects, as shown in FIG. 2. Swelling can be detected as a change in shape between a current scan of the joint as compared with previous scans as a baseline, or by comparing the image to a generic baseline developed from many scans of normal joints. The volume of the swelling can then be calculated utilizing known algorithms. The method involves immobilizing the joint to allow for standardized positioning, for example, by placement into a custom-made mold, imaging the joint from several angles and joining the images into a 3D surface model of the joint. Volume changes can be assessed by comparing differences in surfaces of the model in the region of interest of the joint, by taking cross sections of the model through the area of the joint.

Patients with arthritis often have localized warmth over involved joints, typically evaluated qualitatively by the clinician through direct skin-to-skin contact. This process is subjective and so unreliable that it is no longer used as an outcome measure in most clinical studies.

In the present invention, a thermal infrared (TIR) camera is used to obtain a thermogram of the joint, which is capable of measuring subtle differences in temperature of surfaces with high spatial resolution. A TIR camera converts emitted infrared radiation into electrical impulses that are visualized as either a color or a grayscale image called a thermogram. In addition to making detailed measurements in the examination room, thermal imaging allows quantitative comparison, both spatially and thermally, of a patient's current skin temperature profile with earlier profiles.

Because the absolute temperature of the skin varies from person to person based on external factors, such as ambient air temperature and the patient's level of exertion, the use of an absolute temperature reading is not useful. Instead the measurement of the temperature of the skin in a localized region is compared to the temperature of the skin elsewhere on the same person. For purposes of detecting arthritis in a patient, the use of a heat distribution index (HDI) is useful. The HDI reflects the variation of heat in a joint, and is calculated by choosing a region of interest in the thermogram corresponding to a fixed area of surface anatomy, such as over a joint. The thermal signal is digitized into grey levels. A relative frequency distribution is derived, representing the ratio of the number of pixels which occur at each grey level to the total number of pixels in the area of interest. The HDI represents ±1 standard deviation from the mean frequency. FIG. 3 shows thermograms (a), (b) and (c) of a wrist afflicted with arthritis, the same wrist after receiving treatment and a normal wrist, respectively. The HDI was calculated for each thermogram for a region of interest covering the joint and immediate surroundings. FIG. 3 also shows the typical relative frequency distributions 51, 52 and 53 of temperatures within the joint region. Normal joints (b) and (c) will show a spike 54 at a single temperature, indicating that the temperature of the joint is relatively consistent across the geometry of the joint. Thermograph (a) in FIG. 3 shows the temperature distribution 51 of a joint afflicted with arthritis. Note that the distribution is more spread out, indicating a variation in temperature across the geometry of the joint.

Arthritis patients exhibit limited range of motion, which frequently deteriorates over time. Clinicians measure range of motion either visually or using a goniometer placed against the patient's hand while s/he extends and flexes the joint. This process is subjective because the exact placement of the measuring device is physician-dependent. On the other hand, video-based systems can reliably track body motion and accurately estimate the position of a patient's joints, and these methods can be easily adapted to quantifying the range of motion.

In the case of a rheumatologic examination, tracking of the range of motion of a joint with a video based system can be accomplished by positioning a camera such that its imaging plane is parallel to the joint's plane of motion, thereby imaging the joint in two-dimensions. For example, when viewing the human wrist in profile, it is straightforward to analyze the image to calculate joint angle. For range of motion, measurement of joint angle using cameras has been found to be superior to the clinician's use of a goniometer, since it is non-contact and multiple movements of the patient can be easily captured and averaged in real-time.

Another qualitative examination technique is for the clinician to inspect the skin for erythema (abnormal reddening). As it is not easy for humans to distinguish degrees of erythema unless the differences are pronounced, and for this reason degree of erythema is not often used in evaluating joint inflammation. However, imaging sensors, such as digital cameras, are capable of reliably measuring color differences within a single image as well as over long periods of time. Additionally, due to limitations of the human eye, a clinician's visual observations are restricted to wavelengths in the visible spectrum (400 to 700 nm). However, evidence suggests that the effect of erythema is most observable between 450 and 580 nm (in the visual spectrum) and above 750 nm (in the near-infrared spectrum). For this reason, in the present invention, a multi-spectral camera is used to record skin reflectance over a broad band of wavelengths covering the visible and near-infrared spectrum.

Each of the four sensing modalities produce measurements from which numerical features can be computed. These numerical measurements are distilled into a single score for each type of measurement and into a global score for a combination of the measurements. Representing a global assessment for the joint. To find a correlation between the measured scores and the scores recorded from physical observations by clinicians, a mapping function can be used to determine the mapping from each individual sensor measurement to an individual observable score. The mapped scores for each measurement are then fused to combine individual measurements and scores into a global score.

With the four sensing modalities outlined above, the quantitative measures of the joint examination and their corresponding numerical measures and combined global score will exceed the sensitivity and reliability of the qualitative measures currently used to monitor disease activity and response to treatment. Clinicians should find the objective measurements to be an effective surrogate for direct physical examination. The sensor-based measurements are of the present invention are deterministic, repeatable and consistent over time, and, as such will improve clinical trial outcome measures for arthritis.

DETAILED DESCRIPTION OF THE INVENTION

Existing modalities for measuring outcome in the diagnosis and treatment of arthritis are cumbersome, time-consuming, and often unreliable. In contrast, sensor-based technologies can be quantifiable, reproducible and highly reliable. The present invention establishes ways to apply known sensor technology to the diagnosis of arthritis, as well as the assessment and evaluation of joints. In addition, the same technology can be used to image and measure other areas of the body. The methods are being explained in the context of joint evaluation in arthritis patients merely as exemplars of the technology.

The first modality, 3D imaging utilizing a 3D scanner, is useful for both shape and volume measurement. Shape measurements are useful in comparing recent scans to baseline scans taken during previous examinations. The difference in the shape of the joint can be useful for tracking the effectiveness of therapy and for assessing the presence of swelling in the area of the joint. Volume calculations are useful to see the degree of swelling.

Figure 4:
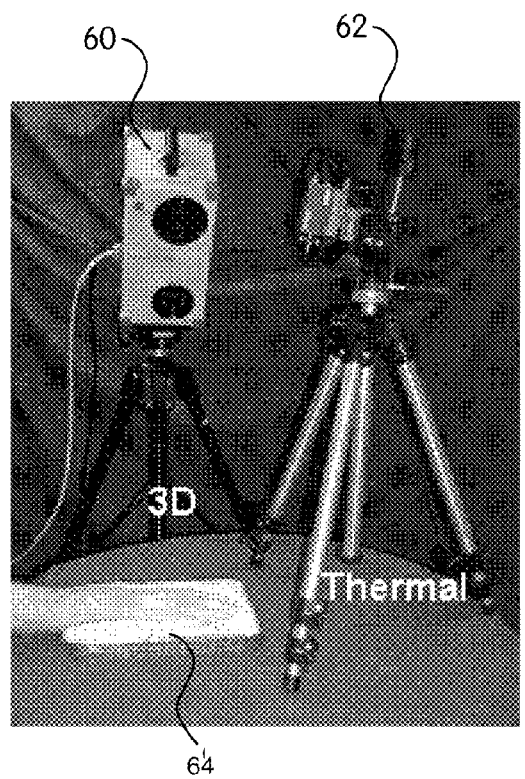
FIG. 4 shows the apparatus for performing 3D scanning and thermal imaging.

In the preferred embodiment of the invention, 3D and thermal images are obtained in a dedicated room in a clinical setting. FIG. 4 shows the setup used to perform the imaging, showing 3D scanner 60, thermal imager 62 and immobilized hand of patient 64. Because 3D image acquisition is not substantially influenced by environmental factors typical of a clinical environment, the environmental conditions of the room will be optimized for thermography, mainly due to limitation of the thermal imager 62. Improvements in thermal imaging technology may make a controlled environment unnecessary. Thermographic imaging will be carried out in a draft-free room with ambient temperature controlled to 20.5±0.5° C. and humidity 50±10%. Subjects were permitted a 15 minutes equilibration period in the room prior to the imaging.

Figure 5:
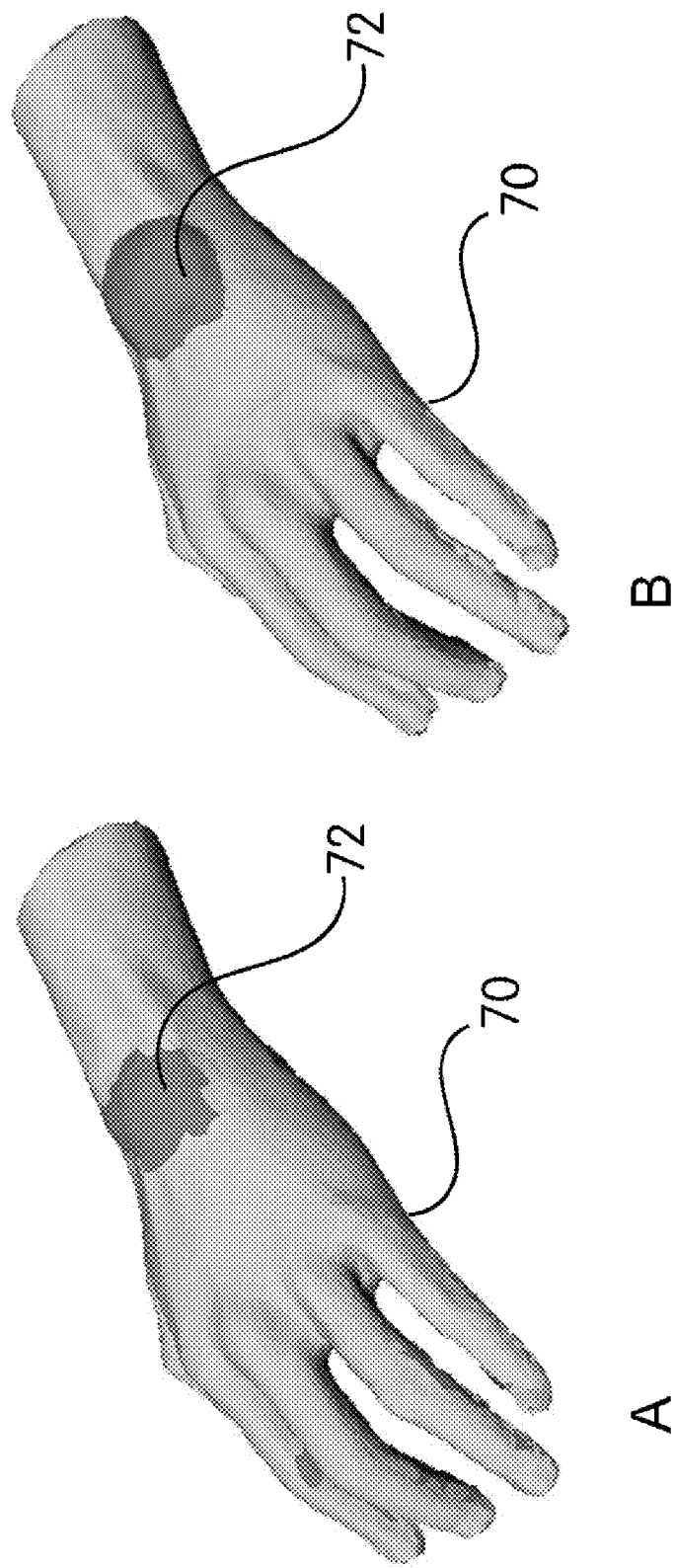
FIGS. 5A and B show a mannequin hand having clay applied thereto to simulate swelling.

The method was developed using the Minolta Vivid 910 3D digitizing scanner. This scanner has an output resolution of 640×480 pixels, and was found to be adequate, however, any 3D scanner having similar or better resolution could be used. A handprint mold was used to stabilize the hand in a standard pose, and scans were obtained from two viewpoints (left and right). A 3D digital model was created from the scans from the scans using software tools available in the art. Additional software was created to automatically compute changes in volume (i.e., swelling). Initial experiments with the apparatus were carried out on a mannequin hand 70, using clay 72 to simulate swelling, as shown in FIG. 5.

Preferably, the end result of the 3D scanning will be a 3D representation of the swelled region, based on both observed changes in shape and calculated changes in volume, as well as a calculated, numerical indicator of the severity of the swelling.

Figure 6:
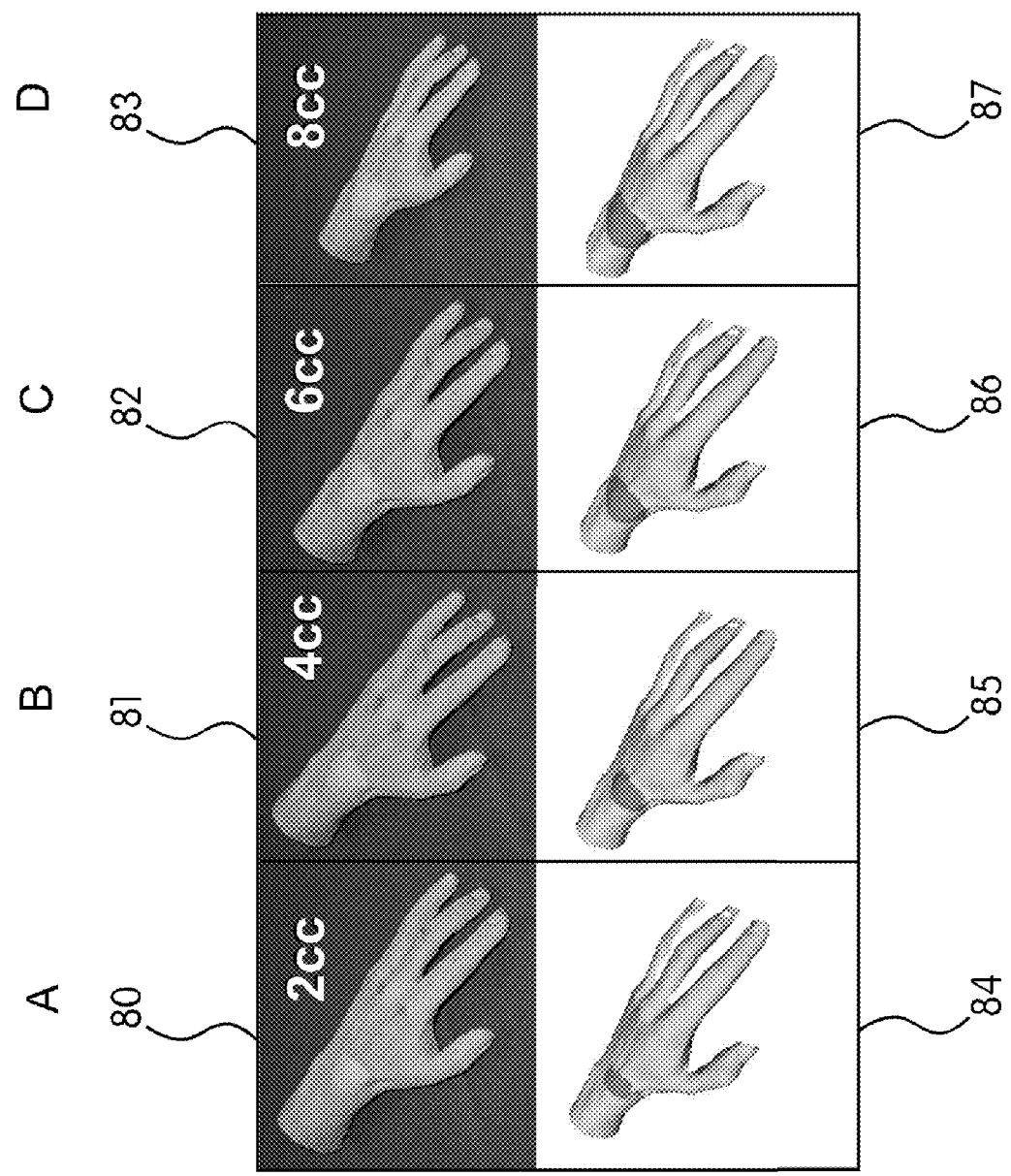
FIGS. 6A, 6B, 6C and 6D show a mannequin hand prepared with varying amounts of clay (top row) to represent swelling, and the corresponding 3D scans of the hand (bottom row), with swelling highlighted.
Figure 7:
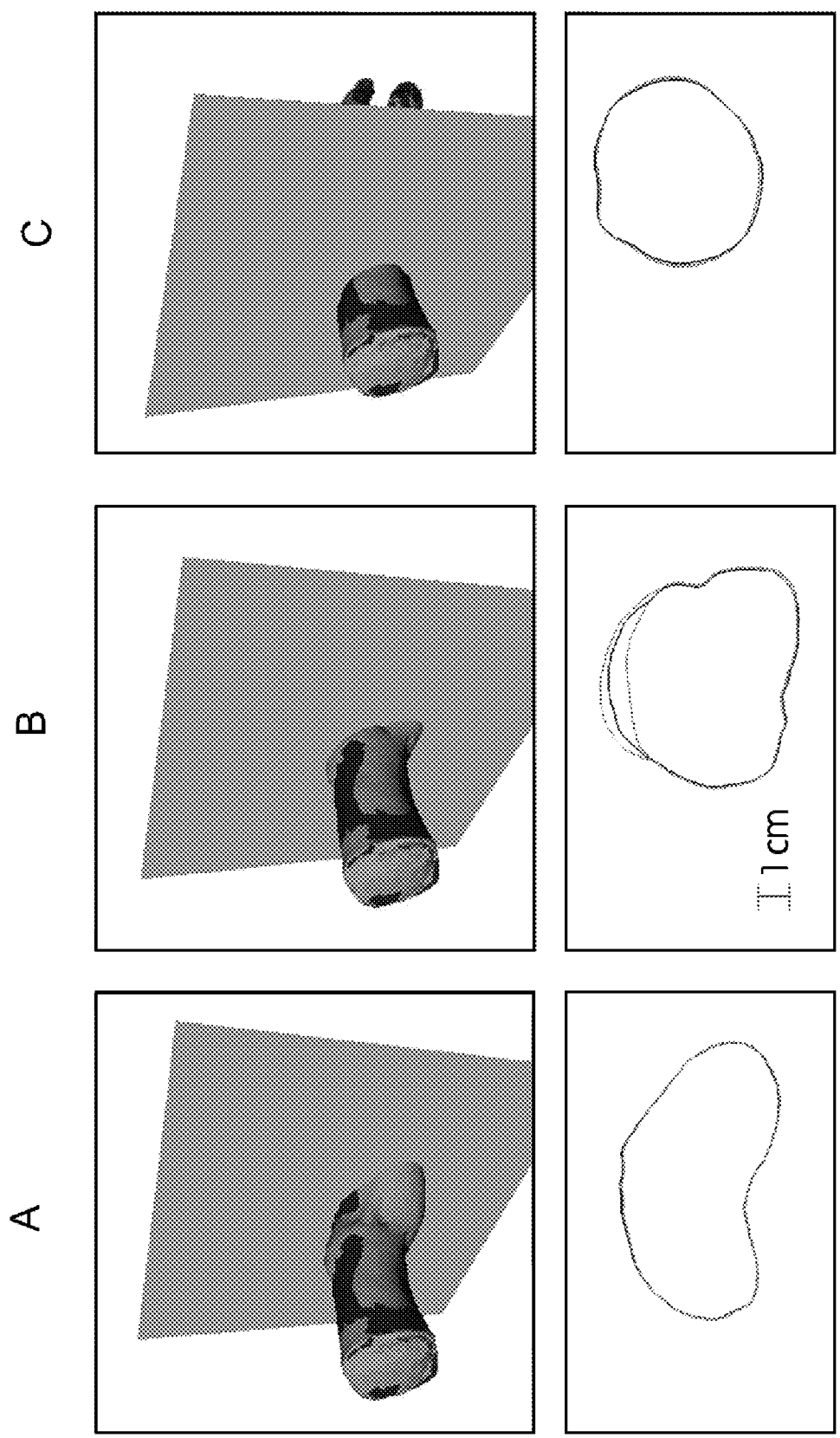
FIGS. 7A, 7B and 7C show models of a hand and corresponding cross sections of a palm, an afflicted wrist and a forearm respectively.

The 3D scanner is capable of sensitive enough to measure swelling volume changes on a mannequin hand and in a patient with arthritis pre- and post-intraarticular corticosteroid injection. A mannequin hand, as shown in the top panels 80-83 of FIG. 6 with 2, 4, 6 and 8 cc of clay applied respectively to simulate swelling was imaged. The corresponding 3D models 84-87 are shown in the bottom panels of FIG. 6. with regions of swelling greater than 1 mm highlighted.

Figure 9:
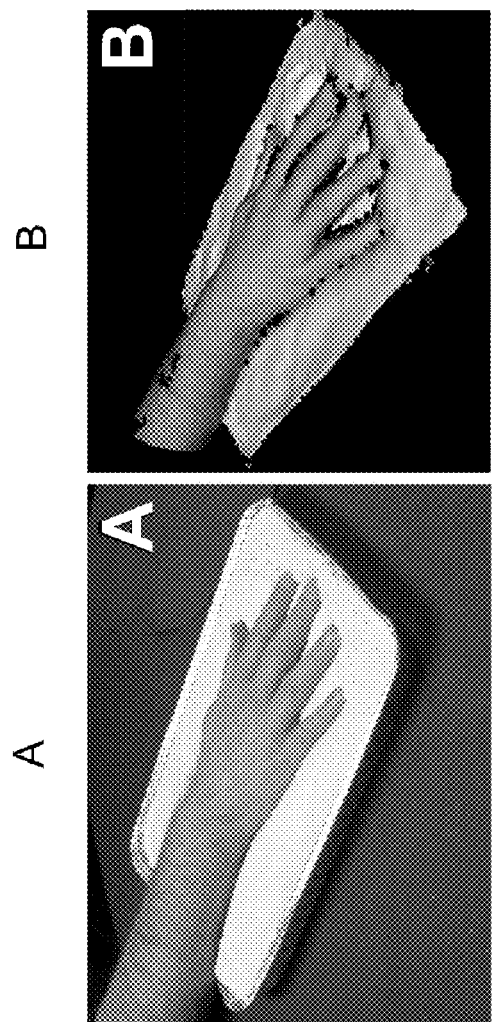
FIG. 9A shows a hand immobilized in a custom-made plaster cast.
FIG. 9B shows the corresponding 3D scan of the hand.

Cross sections of the wrist are then taken to show the degree of the swelling. FIG. 9(a), (b), and (c) show 3D views of the three models superimposed on each other. The reference model is shown with $1^+$ swelling areas and $2^+$ swelling areas highlighted in color. The bottom row of FIG. 9 shows the cross sections obtained at the locations indicated by the grey plane for (a), (b) and (c) respectively. The 3 models show almost exact identity in shape through a cross section of the palm (a) and the forearm (c), while swelling is apparent at the wrist (b).

Figure 8:
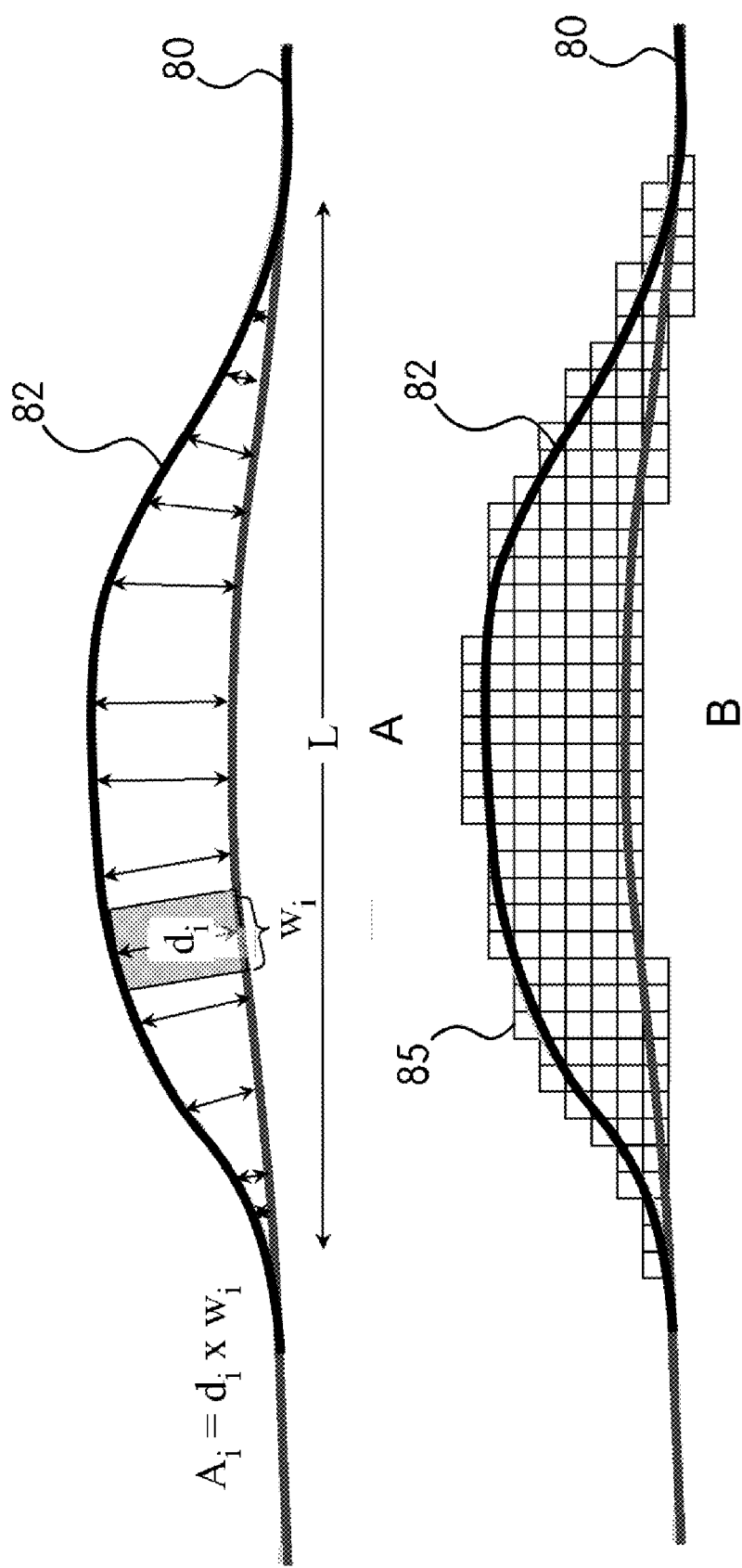
FIGS. 8A and 8B show two mathematical methods used to calculate the volume of the swelled skin surface.

The volume of the swelling can be calculated using one of the methods shown in FIG. 8. The first method, shown in FIG. 8(a), is an approximation for small surface displacements. It involves computing the distance between two surfaces, 80, representing the un-swelled surface of the skin, and 82, representing the swelled surface of the skin, at randomly sampled locations and then summing the areas (volumes in 3D) associated with each sample. This is equivalent to multiplying the length of the swelling region by the average distance between the surfaces in that region. The second method, shown in FIG. 8(b), involves a more sophisticated voxel-based volume estimation method which divides space into small, fixed-sized cubes called voxels 85 (the 3D analog of pixels). The volume estimate is simply the number of voxels that fall between the two surfaces multiplied by the cube volume. Cubes that cross the surface boundaries are handled as special cases by analytically determining the fraction of the cube that falls inside the volume of interest. Additionally, the volume may be computed by taking cross sections at pre-determined intervals across the surface of the swelled area and calculating the area between the boundaries for each cross section, then summing the areas. Many techniques known in the art for calculating the volume may be used.

To stabilize the subject's wrist during the scanning procedure, a plaster handprint mold of the subject's hand and wrist in which the patient's hand is placed during a scanning session may be created, as shown in FIG. 9(a). FIG. 9(b) shows a 3D scan of the hand in the plaster mold.

Although the subject's hands are immobilized during the scanning by the cast, slight changes in the angles of the hand's joints from one session to the next may manifest as a change in hand shape even if there is no change in swelling. While the effect is small, addressing the issue directly will lead to improved sensitivity in swelling measurement over our baseline approach. The method of the present invention uses two well-established methods to address hand motion. The first method, local registration, capitalizes on the fact that it is not necessary to register the entire hand in order to make local surface shape comparisons. For example, if only wrist swelling is of clinical interest, only the region around the wrist needs to be aligned. The method includes designating 10 regions of interest in general hand anatomy, with surface areas ranging from 1 to 100 cm$^2$ (for example, the ulnar and radial styloids, MCPs and PIPs).

The second method, pose recovery, involves explicitly recovering joint angles using a hierarchical, part-based registration technique that aligns corresponding features (e.g., forearm, palm, and finger segments) between two hand models. For small changes in joint angles, particularly ones that do not significantly alter the appearance of the hand (small variations in the spreading of the fingers, for example) this method is robust and reliable. Using this technique, we are able to algorithmically recover the joint angles of the major joints in the hand (i.e., wrist and fingers). A combination of the two motion compensation approaches may provide the best results. For example, a combination of the local registration of two regions (one located on the forearm and one covering the dorsal hand surface) with explicit recovery of the joint parameter at the wrist.

Figure 1:
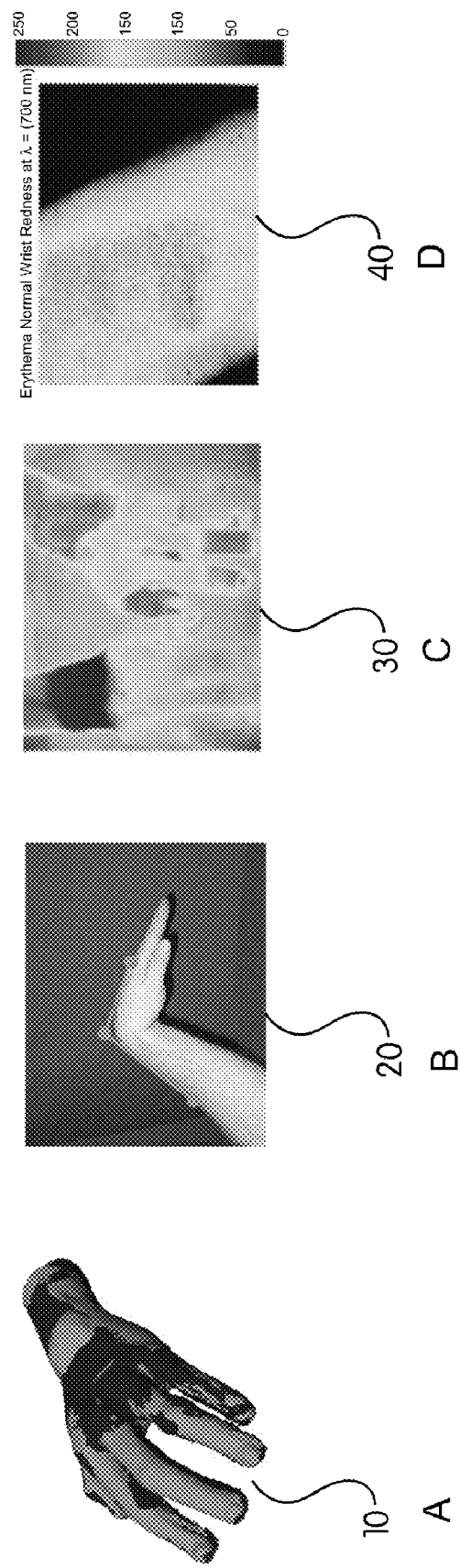
FIGS. 1A, 1B, 1C and 1D show the four sensing modalities.
Figure 2:
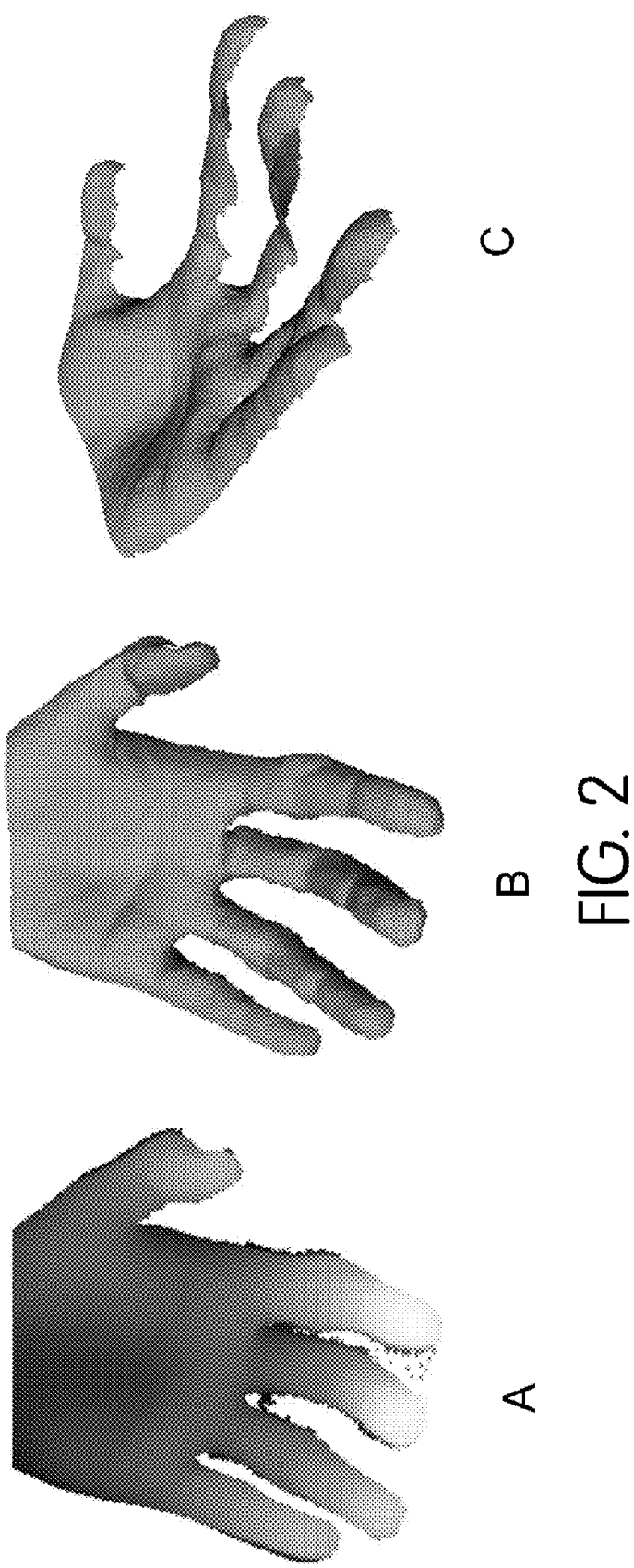
FIGS. 2A, 2B and 2C show examples of a 3D scan of a human hand.
Figure 3:
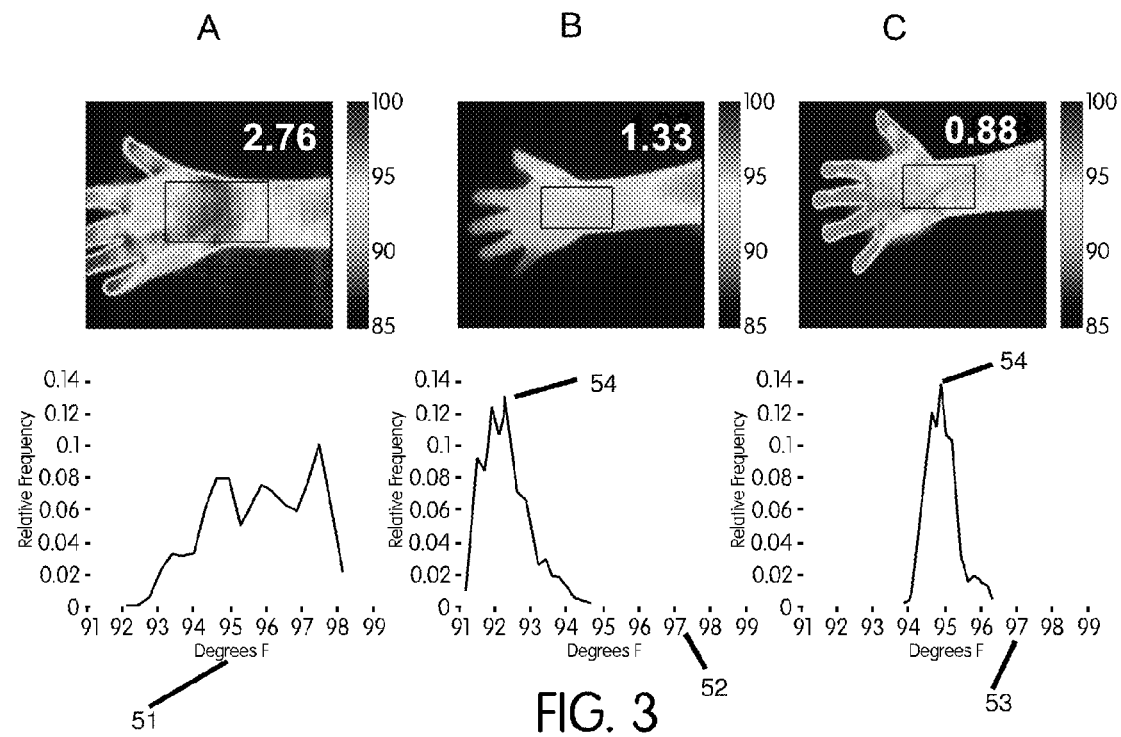
FIGS. 3A, 3B and 3C show thermograms or a wrist showing the temperature distribution for an afflicted wrist, a treated wrist and a normal wrist.

Thermal imaging is useful for purposes of assessing arthritis in the joints because of the abnormal heat distribution patterns observable in joints afflicted with the disease. Normal joints will have a constant and narrow temperature range over the geometry of the joint, while a joint afflicted with arthritis will exhibit "hot spots" or areas or higher and lower temperature over the geometry of the joint. This can be seen in FIG. 3. FIG. 3(c) shows a normal wrist joint, having a constant temperature over its entire surface. FIG. 3(b) shows a wrist after treatment, also having a range of temperatures over its surface.

Figure 10:
FIG. 10 shows a thermal imaging camera.
Figure 11:
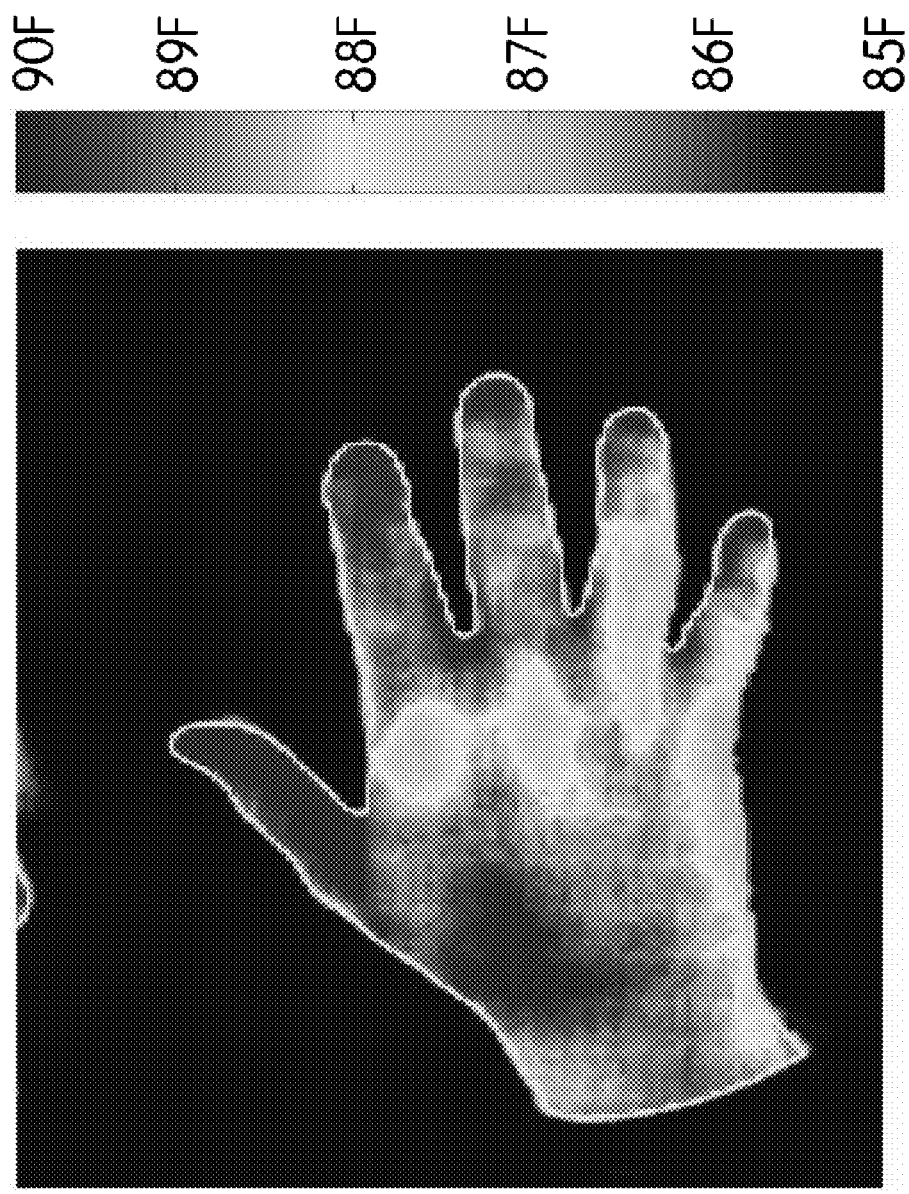
FIG. 11 shows a thermogram of a normal hand and wrist obtained with the camera of FIG. 10.

To capture the thermograms, an Alpha camera from Indigo Systems, as shown in FIG. 10, or any equivalent camera, may be used. The Alpha camera is a microbolometer camera which generates 320×240-pixel thermograms at video rates via a firewire framegrabber. The camera has a temperature sensitivity of <0.5° C. FIG. 11 shows a typical thermogram of a normal hand and wrist obtained with the Alpha camera. Note the normal thermal pattern of joints in which the skin over the wrist and MCP joints is constant or slightly cooler than other parts of the hand. Patients with arthritis have an inversion of their thermal image, with an increased relative temperature over the involved joint. The camera was placed at a distance of 1 meter from the joint being imaged.

Thermal imaging software, such as ThermaSTAT by WinSoft of Santa Ana, Calif. or general purpose image processing software, such as MatLab by The MathWorks of Natick, Mass. may be used for analyzing the images. To obtain absolute temperature measurements, two temperature controlled calibration targets are placed into the camera's field of view. Absolute temperature throughout the thermogram can then be computed by linearly mapping the pixel intensities based on the pixel intensities for the two known temperature targets. While this camera is adequate for purposes of this invention, other commercially available thermal cameras, such as the Compix Model 220, have greater sensitivity, simpler operation, and do not require calibration targets. The Model 220 has a sensitivity of <0.1° C. and can be controlled by a laptop computer via a USB interface.

To verify the reproducibility of thermal imaging of the wrist, a sequence of five wrist thermograms was acquired in rapid succession from a normal subject. The hand and wrist were kept immobile using the same plaster handprint mold described for the 3D imaging studies above. The variation in temperature value within a 20×20-pixel window on the wrist was then analyzed. The average standard deviation within the window was 0.13° F. This corresponds to an intra-class correlation coefficient of ICC=0.98 when measuring temperatures at 400 pixels with repeated scans.

The predominant effect on temperature measurement is variability in temperature over time due to uncontrollable internal factors (metabolic rate, caloric intake, etc.) within the subject. As described above, two measures have been developed for quantifying abnormal joint temperature: the thermographic index (TI) and the heat distribution index (HDI). The TI reflects the average absolute temperature within a manually-specified region of interest, while the HDI reflects the variation of heat over a joint. HDI is calculated by first choosing a region of interest on the thermogram corresponding to a fixed area of surface anatomy over the joint. The thermal signal is digitized into grey levels. A relative frequency distribution is derived, representing the ratio of the number of pixels which occur at each grey level to the total number of pixels in the area of interest. The HDI represents ±1 standard deviation from the mean frequency. Based on experimentation, we have found that the absolute temperature varies much more than relative temperatures. The TI varied by as much as 10° F. in a single day, while the HDI was typically between 0.8 and 1.1° F. The standard deviation of the 10 HDI values was 0.524° F. As a result, we have concluded that the HDI is a much more effective measure of probable joint disease than the TI. Preferably, the end result of the thermography will be a color coded thermal map showing the distribution of temperatures and a numerical calculation of the temperature above various pre-determined thresholds.

It was also observed that a correlation exists between the degree of swelling as measured by the 3D imaging and the HDI. Therefore, in addition to detecting overall changes in swelling and temperature, the information obtained from 3D scanning and 2D thermography can be combined to provide an overall view of the diseased joint. The 2D thermal image can be texture-mapped onto the 3D hand model or the 3D hand model can be projected onto the 2D thermal image. These techniques allow the integration of the information from 3D imaging and thermography to determine whether the subregions of change in swelling and temperature are consistent with each other. The key to performing either transformation is to determine the position of the thermal camera relative to the hand. A virtual camera is then placed in the 3D hand model's coordinate system at the same position relative to the hand as the real thermal camera was originally located. Once the camera position is known, any pixel in the thermal image can be matched to its corresponding point on the 3D hand model through simple geometry. To texture-map the thermal image onto the 3D hand model, the thermal image is projected onto the hand model from this camera position, and the 3D surface is colored to reflect the temperature levels from the thermal image. To project swelling levels from the 3D model onto a thermal image, the 3D hand surface is color coded according to swelling level and rendered (i.e., displayed) from the viewpoint of the thermal camera. Pattern recognition algorithms can then be applied either to the 2D images or the 3D surface. Each approach has tradeoffs. Although analyzing the 2D images is simpler, because the data is arranged on a regular grid, the analysis is limited to surfaces that can be seen from a single viewpoint. For example, if swelling is detected on the sides of the wrist, this information would be lost when projected to an image as seen from directly above the wrist. Performing the analysis in 3D overcomes this problem, but the algorithms must be adapted to operate on surface meshes, which are not regular grids.

In a like manner, the 3D surface model can also be combined with the near-infrared spectral image to correlate the areas of swelling with areas displaying erythema. In other embodiments, any combination of the 3D surface model, the thermogram and the near-infrared or visual image may be combined to show a correlation between the symptoms detectable using each scanning modality.

The combination of the results of the 3D scanning and the 2D thermography into a composite disease activity index having both volume and temperature components. By first conceptualizing individual patients' (1) changes in volume of swelling and (2) changes in HDI as two-dimensional (x, y)-coordinates, then visualizing them on a plane, it follows that pattern recognition and cluster analysis approaches can be applied to arthritis treatment response. The two dimensions can be standardized so that they have the same scale. A principal components analysis can be performed as one approach. The first principal component is the linear combination of the change in volume and the change in HDI coordinates along which the arthritis patients most differ, and is a good candidate for a composite index. If most of the variation is explained by the first principal component, then the bivariate plot of (x, y) points would look like a regression scatter plot, with the points distributed around the first component line. The first component is the projection along this line. This approach has the potential for distinguishing different treatment responses with a simple linear index. If a substantial amount of variation is not explained by the first principal component, this indicates that both the change in volume of swelling and change in HDI are required to characterize treatment response. The full two-dimensional display of points needs to be used in that case. Discriminate analysis (both linear and quadratic), k-means and other cluster analysis, neural network and other pattern recognition methods can also be applied to potentially identify distinct treatment response groups.

Figure 12:
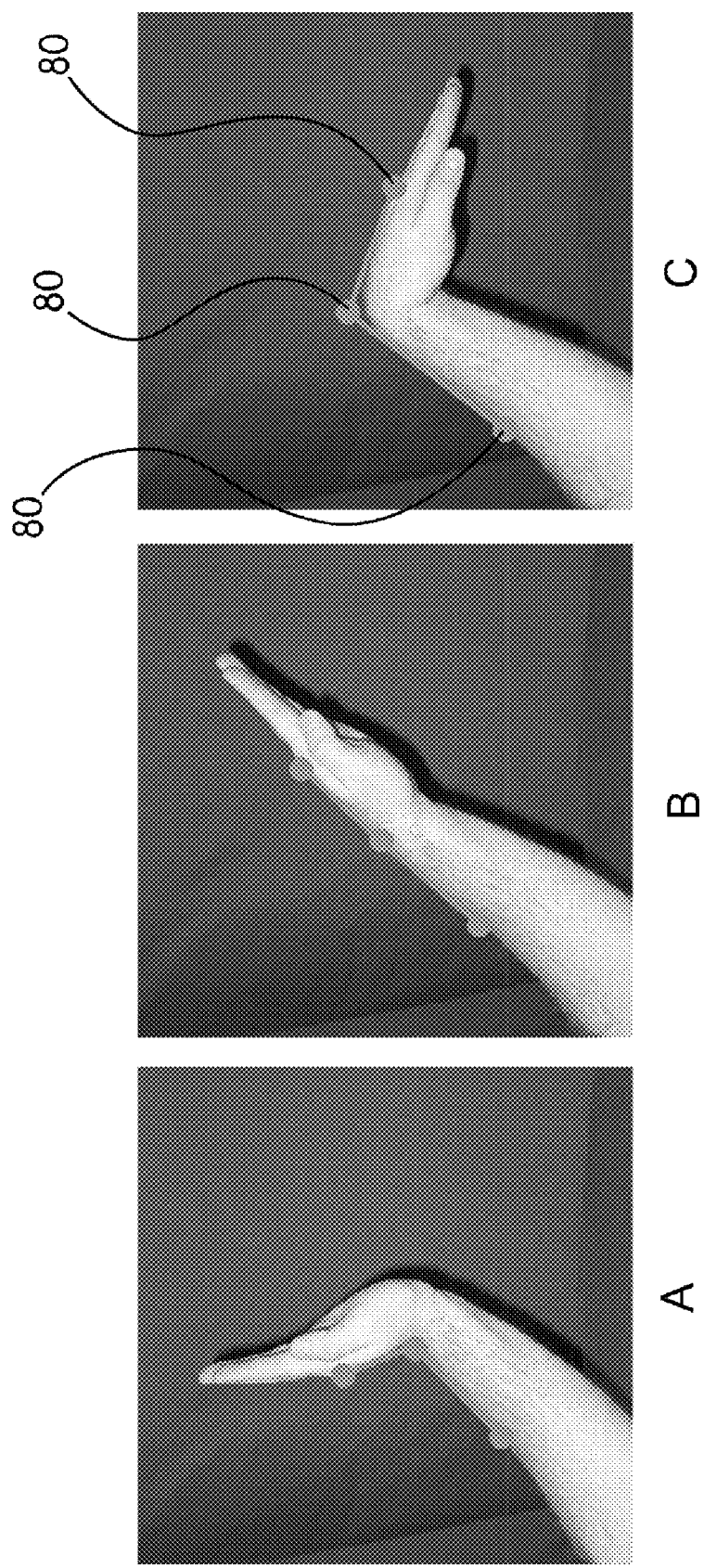
FIGS. 12A, 12B and 12C show a wrist being images as it moves through a range of motion.

The third modality is of range of motion. A standard, commercially available digital video camera with a real-time interface to a computer will be used. Customized tracking software will be used for tracking the markers in the video. In trials using a side-positioned consumer-grade digital camera (Olympus C-2000), a series of photographs were taken as a test subject moved his hand through its entire range of motion, as shown in FIG. 12. A blue background was used to simplify segmentation of the hand from the background. For this experiment, corresponding points in all images were manually identified, however, markers 80 can be used and can automatically be tracked using software. Using the marked points, the joint angles can be directly measured from the images. Preferably, the end result of the range of motion mode will be a numerical indicator of the extrema in both the positive and negative directions of the motion, as well as an indicator of total range (difference of extrema).

The final modality is erythema measurement. As previously stated, visual observations are restricted to wavelengths in the visible spectrum (400 to 700 nm), but it has also been observed that the effect of erythema also has a component in the near-infrared spectrum, at wavelengths above 750 nm. Therefore, a camera capable of recording images in the near-infrared spectrum, as well as in the visible spectrum is used. The multi-spectral imaging technology is based on the acousto-optic tunable filter (AOTF), a technology that optimally exploits remote sensing in the multi-spectral domain by allowing tuning to discrete wavelengths or ranges of wavelengths. Currently available spectro-polarimetric (SPI) cameras, an example of which can be seen in FIG. 13, have been optimized for near infrared operation. This is exactly the spectral region of likely greatest impact for the characterization of erythema in skin. Preferably, the measurement of the erythema will result in a color map of the affected areas as well as a calculated numeric value of the surface area above various pre-defined thresholds.

Figure 13:
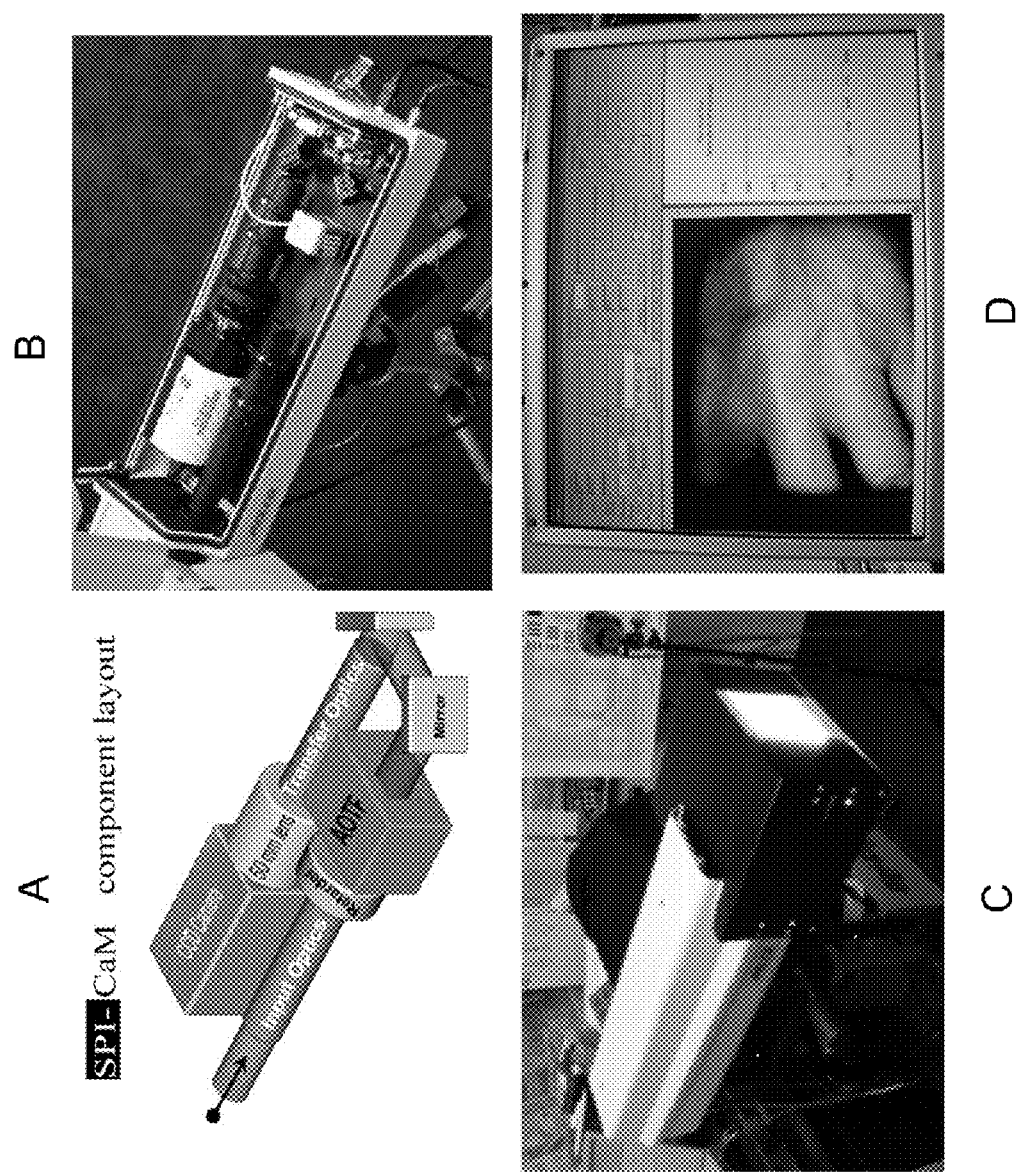
FIGS. 13A, 13B and 13C show a spectro-polarimetric (SPI) camera
FIG. 13D shows an image of a hand.

FIG. 13 shows the spectro-polarimetric imager (SPI) to be used in the preferred embodiment of the invention. The SPI will extend a color digital camera's three (red, green, blue) filtering to over 100 bands from the blue (450 nm) to deep into the near infrared (1100 nm). The SPI's broad spectral response, its ability to be tuned to specific wavelengths, and its capability for numeric spectral analysis make it an ideal research instrument for determining how best to detect and quantify erythema. The SPI has a spectral resolution of 3 nm at 600 nm. Using 8 bit digital logic, the best intensity accuracy is in the range of 1%. FIG. 13 shows the components of the SPI camera head, including the integrated controller/driver board that provides all electronic functionality except for the PC computer used for image processing and analysis. Lamps that are installed to the faceplate cast broadband illumination onto a 4" by 4" area and reflected light is captured through custom optics. An image of a hand is also displayed in FIG. 13.

Figure 14:
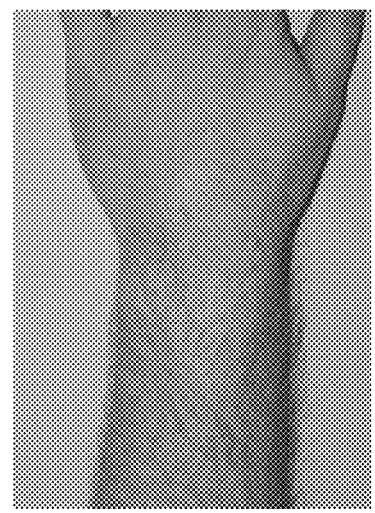
FIG. 14A shows a normal hand.
FIG. 14B shows a hand warmed by a towel to produce redness.
FIG. 14C shows a graph of the reflectance of the hand as a function of wavelength.
Figure 14:
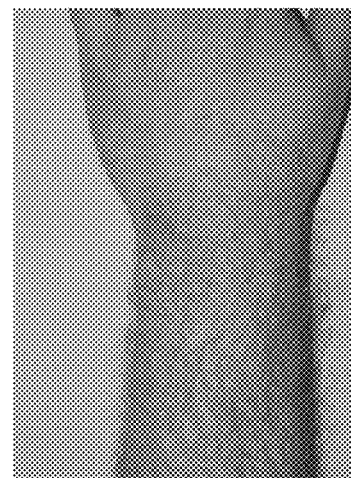
Figure 14:
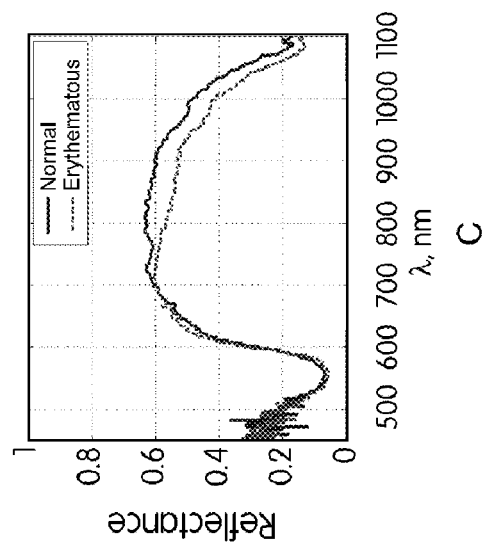

The intensity and spectral shape of reflected light directly manifest properties of the surface of the skin; they can be readily compared to normative standards and longitudinally on a patient-specific basis. As shown in FIG. 14, as an example of this modality, two multi-spectral scans of the wrist of a test subject were obtained, one scan under normal conditions (a) and one after the wrist had been reddened using a warm towel (b). The reflectance versus wavelength graph is shown as (c). Notice that the reflectance of the erythematous hand rises slightly above that of the normal hand in the region around 630 nm (the visible spectrum), due to the visible reddening of the skin. However, a much more significant difference occurs in the near infrared wavelengths above 800 nm, where the reflectance of the erythematous hand decreases compared to the normal hand.

Preferably, one embodiment on the invention will allow the interactive presentation of composite data. Texture mapping is an established technique to map 2D images (such as the temperature and erythema profiles) onto the surface of a corresponding 3D model. Other techniques known in the art for combining images, including both 3D and 2D images, may be used. The result would allow the physician to interact with several forms of data simultaneously. For example, the physician could ask the system to highlight all points that are swollen AND 1° F. warmer than the others AND erythematous. We believe that this composite representation will be valuable because the clinician actually receives several data channels simultaneously, just as in the traditional physical examination.

With respect to the development of a global assessment mechanism for determining the overall health of a joint, each of the 4 sensing modalities produces a measurement from which numerical features will be computed. These numerical features are then distilled into a single score for each modality. These single scores are then weighted and combined, in any combination, to produce a summary, global score of the joint health. However, it is desirable that this global score correlate in some manner to the global assessments used by clinicians currently.

Figure 15:
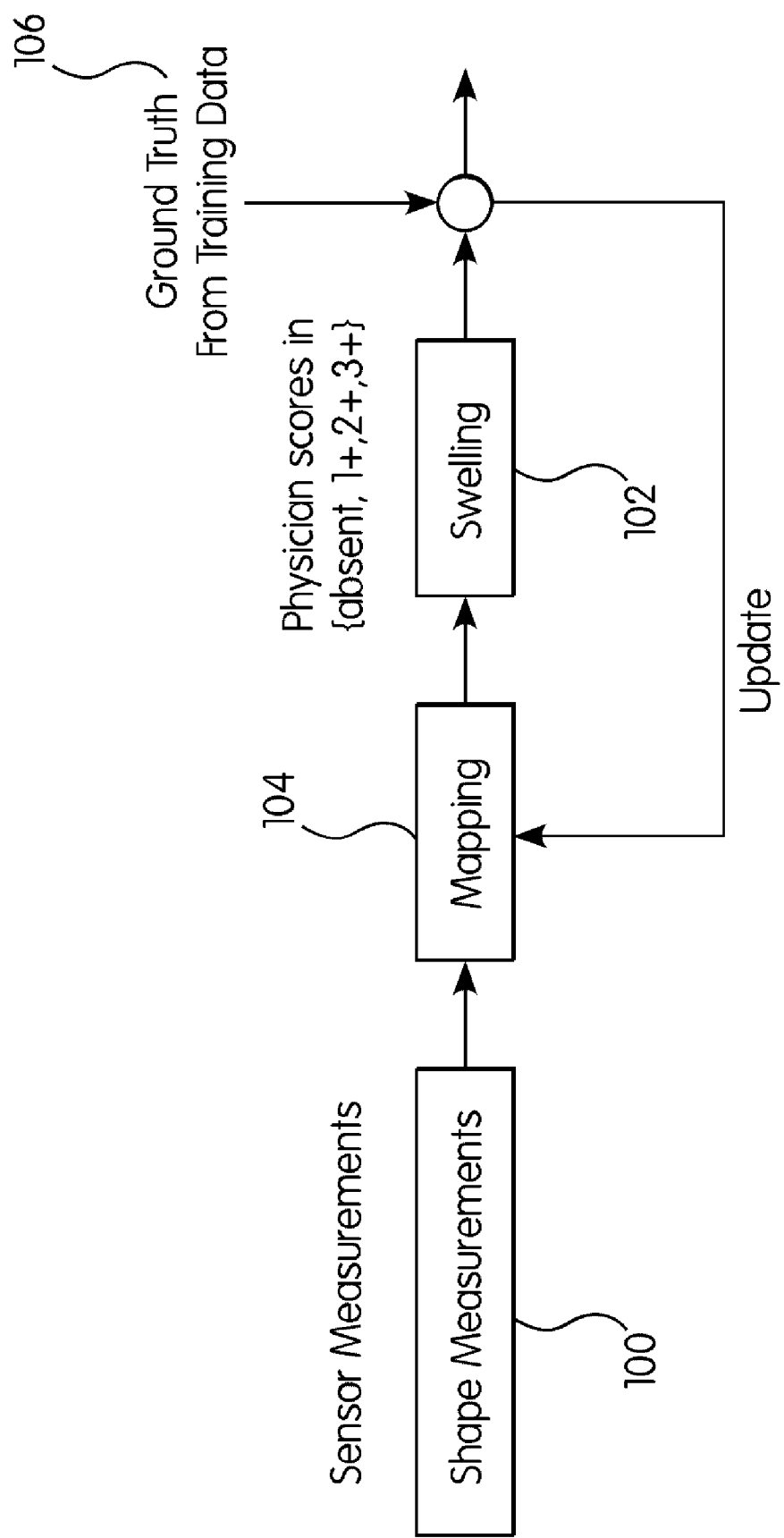
FIG. 15 shows a method for mapping measured sensor outputs to physician's assessments of the same condition.

To accomplish this, a mapping 104, shown in FIG. 15, between actual sensor measurements 100 and actual clinician scores 102 subjectively provided as the result of an examination can be used. The mapping problem is an instance of classical function regression in which one determines a function that maps one data set (sensor measurements 100) to another (physician scores 102) such that the error between the score output by the mapping and the "true" score as recorded from training data 106 is minimized. Many techniques well known in the art may be used for this type of function approximation, for example, kernel-based regression and neural networks.

Figure 16:
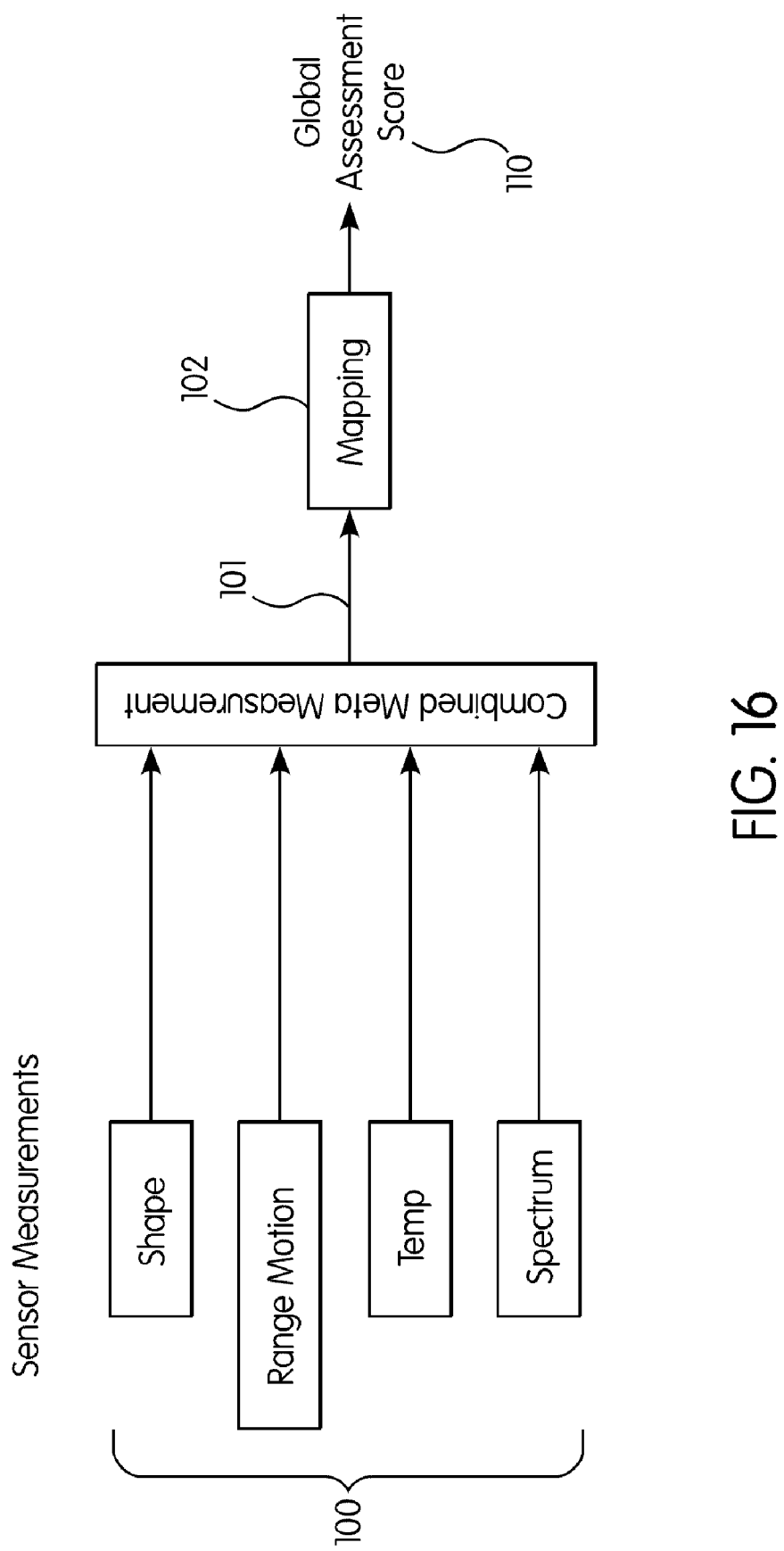
FIG. 16 shows s single-stage fusion method for performing the mapping of FIG. 15.

Sensor-based measurements can be fused into a global score 110, as shown in FIG. 16. For multiple measures, established statistical techniques can be used to optimally combine these measurements into a composite score. The measured scores can then be compared with a score 102 provided by a plurality of clinicians, using a standard visual analog scale, which represents the summation of that physician's overall assessment of the severity of disease in a given joint.

Figure 17:
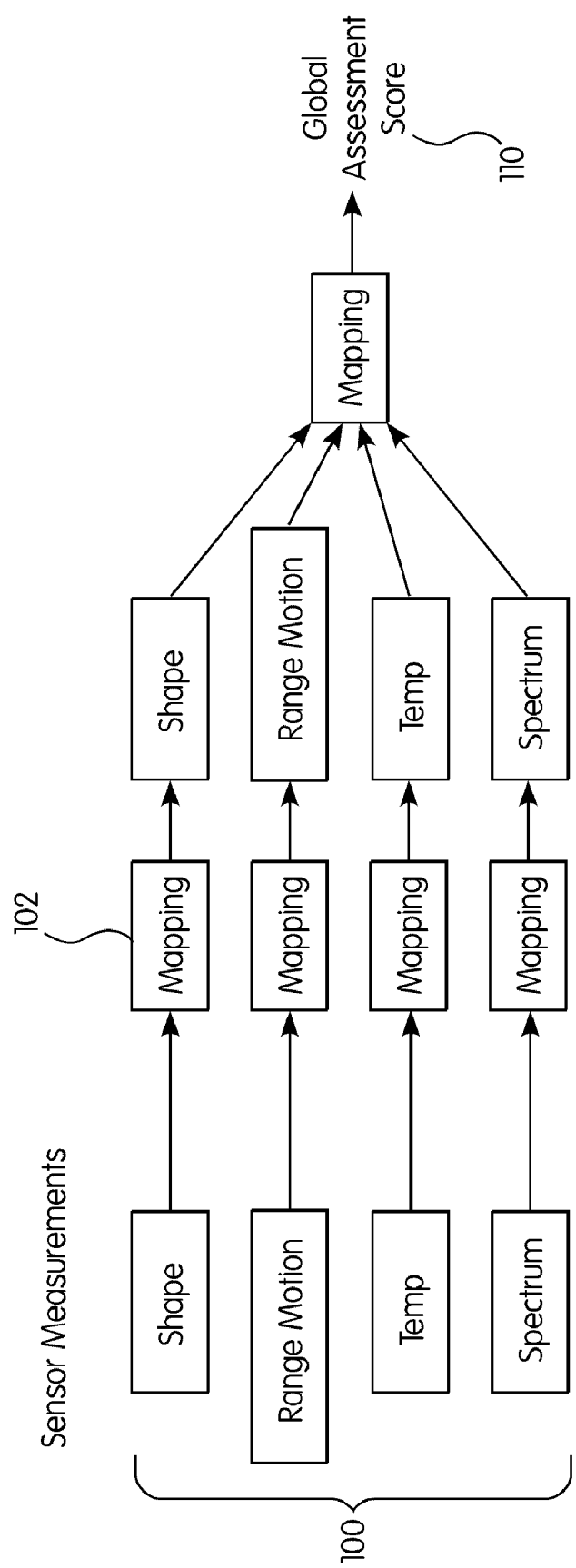
FIG. 17 shows a multi-stage fusion method for performing the mapping of FIG. 15.

There are two approaches for determining a global score from sensor measurements: single-stage fusion, as shown in FIG. 16, and multi-stage fusion, as shown in FIG. 17. In single-state fusion, all of the sensor measurements 100 are combined into a single, "meta-measurement" 101 and a mapping 102 between the meta-measurements and a global assessment score 110 is derived that minimizes the error over the training data using the same function approximation techniques as described above. This approach has the advantage that all the sensor measurements are integrated directly. One drawback is that it does not use the intermediate scores currently used by the physicians. In multi-stage fusion, as shown in FIG. 17, each of the sensor measurements 100 is mapped 101 separately to a physician score 102, and, in a second stage, the physician scores are combined 108 into a single global assessment score 110. Here again, the error between the output scores and the ground truth score from training data is minimized. The advantage of this approach is that the training procedure can automatically determine the relative weights that should be used for combining sensor measurements. Many strategies can be used for this type of training, such as boosting, or stacked generalization.

Many other applications of the scanning technology and methodology described herein exist. For example, the 3D scanning method can be used to assess or screen for skin cancer or other skin conditions, such as scleroderma or as a screening method for breast cancer. For this application, a 3D model of a skin lesion or nevus is created and a follow-up 3D scan is taken at a later time, such that the two scans can be compared to each other for change in size and shape. Such a method would allow for the precise measurement of the change in size or shape of the lesion. In addition, it may also be useful to combine, as previously described, different modalities, for example, 3D with thermal imaging or near-infrared imaging, to provide sensitivity and specificity.

The described application, illustrations, layouts and equipment selections used herein are exemplary in nature only and are not meant to limit the scope of the invention, which is embodied in the claims which follow. Also, various modifications could be made to the embodiments described without departing from the spirit and scope of the invention.

We claim:

1. A method of screening for skin abnormalities comprising the steps of:
    imaging a skin lesion with a three dimensional scanner from one or more angles to create one or more images;
    combining said images to create a first three dimensional surface model of said lesion;
    repeating the imaging and combining process at a later time to create a second three dimensional surface model of said lesion;
    comparing said first and said second three dimensional models to determine if said lesion exhibits a change in size or shape;
    imaging said skin lesion with a near-infrared imager;
    comparing the reflectance of said skin lesion with a reference near-infrared image of said skin lesion;
    determining the difference in reflectance between said skin lesion and said reference image at near-infrared wavelengths;
    combining said near-infrared image with said second three dimensional surface model;
    determining any differences in shape between said second three dimensional surface model and said reference model; and
    correlating said differences in reflectance with said differences in shape.

2. A method of assessing the health of a body part comprising the steps of:
    imaging said body part with a three dimensional scanner from one or more angles;
    combining said images to create a three dimensional surface model;
    comparing said three-dimensional surface model to a reference model;
    determining any differences in shape between said three-dimensional surface model and said reference model;
    correlating said differences in reflectance with said differences in shape;
    imaging said body part with a near-infrared imager;
    comparing the reflectance of said body part with a reference near-infrared image of said body part;
    determining the difference in reflectance between said body part and said reference image at near-infrared wavelengths; and
    combining said near-infrared image with said three dimensional surface model.

3. The method of claim 2 further comprising the steps of:
    imaging said body part with a thermal imager;
    determining the distribution of temperatures across said body part; and
    combining said thermal image with said three dimensional surface model.

4. The method of claim 3 further comprising the steps of:
    determining any differences in shape between said three dimensional surface model and said reference model; and
    correlating said temperature distribution with said differences in shape.

5. The method of claim 4 further comprising the step of rendering a visual display of said combined thermal image and said three dimensional surface model, said rendered image having said differences in shape and temperature distribution highlighted.

6. The method of claim 3 further comprising the steps of:
    calculating any change in volume between said three dimensional surface model and said reference model; and
    correlating said temperature distribution with said change in volume.

7. The method of claim 6 further comprising the step of rendering a visual display of said combined thermal image and said three dimensional surface model, said rendered image having said change in volume and temperature distribution highlighted.

8. The method of claim 7 further comprising the step of rendering a visual display of said combined near-infrared image and said three dimensional surface model, said rendered image having said differences in shape and reflectance highlighted.

9. The method of claim 7 further comprising the steps of:
calculating any change in volume between said three dimensional surface model and said reference model; and correlating said differences in reflectance with said change in volume.

10. The method of claim 9 further comprising the step of rendering a visual display of said combined near-infrared image and said three dimensional surface model, said rendered image having said change in volume and difference in reflectance highlighted.

11. The method of claim 2 further comprising the steps of:
imaging said body part with a visual imager as said body part passes through a range of motion; and
combining said visual images with said three dimensional surface model.

12. The method of claim 11 further comprising the steps of:
determining any differences in shape between said three dimensional surface model and said reference model; and
rendering a visual display of said combined visual image and said three dimensional surface model having said differences in shape highlighted.

13. The method of claim 11 further comprising the steps of:
calculating any changes in volume between said three dimensional surface model and said reference model; and
rendering a visual display of said combined visual image and said three dimensional surface model having said changes in volume highlighted.

14. The method of claim 2 further comprising the steps of:
determining any differences in shape between said three dimensional surface model and said reference model;
calculating any changes in volume between said three dimensional surface model and said reference model; and
correlating said differences in shape with said changes in volume.

15. The method of claim 14 further comprising the step of rendering a visual display of said body part having said differences in shape and said changes in volume highlighted.

16. A method of assessing the health of a body part comprising the steps of:
imaging said body part with a thermal imager to obtain a thermal image;
determining the distribution of temperatures across said body part;
imaging said body part with a near-infrared imager to obtain a near-infrared image;
comparing the reflectance of said body part with a reference near-infrared image of said body part;
determining the difference in reflectance between said body part and said reference image at near-infrared wavelengths;
combining said near-infrared image with said thermal image; and
rendering a visual display of said combined near-infrared image and said thermal image, said rendered image having said differences in reflectance highlighted and further having different temperatures highlighted differently.

17. The method of claim 15 further comprising the step of comparing said distribution of temperatures to the distribution of temperatures from a reference thermal image.

18. The method of claim 16 further comprising the step of rending a visual display of said temperature distribution, having different temperatures highlighted differently.

19. The method of claim 16 further comprising the steps of:
imaging said body part with a visual imager as said body part passes through a range of motion; and
combining said visual images with said thermal image.

20. The method of claim 19 further comprising the step of rendering a visual display of said combined visual images and said thermal image, said rendered display having different temperatures highlighted differently.

21. A method of assessing the health of a body part comprising the steps of:
imaging said body part with a near-infrared imager;
comparing the reflectance of said body part with a reference near-infrared image of said body part;
determining the difference in reflectance between said body part and said reference image at near-infrared wavelengths;
rendering a visual display of said near-infrared image having said differences in reflectance highlighted;
imaging said body part with a visual imager as said body part passes through a range of motion to obtain a visual image based on range of motion; and
combining said visual images based on range of motion with said near infrared image.

22. The method of claim 21 further comprising the step of rendering a visual display of said combined near-infrared image and visual image, said display having said differences in reflectance highlighted.

* * * * *

UNITED STATES PATENT AND TRADEMARK OFFICE
CERTIFICATE OF CORRECTION

| | | |
|---|---|---|
| PATENT NO. | : 7,734,077 B2 | Page 1 of 1 |
| APPLICATION NO. | : 12/395912 | |
| DATED | : June 8, 2010 | |
| INVENTOR(S) | : Hirsch et al. | |

It is certified that error appears in the above-identified patent and that said Letters Patent is hereby corrected as shown below:

Col. 14, line 13, please change "claim 15" to --claim 16--

Col. 14, line 41, please change "near infrared" to --near-infrared--

Signed and Sealed this
First Day of March, 2011

David J. Kappos
*Director of the United States Patent and Trademark Office*